United States Patent [19]

Lewis et al.

[11] 4,431,741

[45] Feb. 14, 1984

[54] HYPOTHYROID CONTROL SERUM

[75] Inventors: Jerome Lewis, Framingham; George H. Parsons, Jr., Arlington, both of Mass.

[73] Assignee: Baxter Travenol Laboratories, Inc., Deerfield, Ill.

[21] Appl. No.: 331,479

[22] Filed: Dec. 17, 1981

[51] Int. Cl.³ ............................................. G01N 33/54
[52] U.S. Cl. ........................................ 436/500; 436/8; 436/811; 436/817
[58] Field of Search ..................................... 436/500, 8

[56] References Cited

U.S. PATENT DOCUMENTS

| | | |
|---|---|---|
| 3,666,854 | 5/1972 | Eisentraut ................................ 424/1 |
| 3,776,698 | 12/1973 | Eisentraut . |
| 3,911,096 | 10/1975 | Chopra ................................... 424/1 |
| 3,922,145 | 11/1975 | Turner . |
| 3,922,145 | 11/1975 | Turner et al. ........................ 436/16 |
| 3,928,553 | 12/1975 | Hollander . |
| 4,108,974 | 8/1978 | Wegfahrt et al. ....................... 424/1 |
| 4,110,076 | 8/1978 | Marcherita ............................. 424/1 |
| 4,111,656 | 9/1978 | Margherita ............................ 424/1 |

*Primary Examiner*—Benjamin R. Padgett
*Assistant Examiner*—M. Moskowitz

[57] ABSTRACT

A hypothyroid control serum for use in assay of thyroid function of serum with a reagent antiserum, said control comprising (a) serum from which triodothyronine and thyroxine have been stripped and (b) low-affinity antibody against triiodothyronine.

9 Claims, No Drawings

HYPOTHYROID CONTROL SERUM

This invention relates to hypothyroid control serum for use in thyroid function assay of serum with reagent antiserum against triiodothyronine (T3), and to a method of making such control serum.

It is well-recognized that various physiological and pathophysiological states, apart from thyroid disease itself, can influence the assessment of thyroid function, particularly the diagnostic significance of serum total thyroxine (T4) and T3 hormone concentrations. These factors mainly act by increasing or decreasing the concentration of thyroxine binding globulin (TBG) or by competing with T4 or T3 for binding sites on TBG, thereby decreasing their availability to the hormones. Changes in the total concentration of TBG binding sites for T4 and T3, in the absence of thyroid disease, are associated with parallel changes in serum total T4 and T3 concentrations. Hence, increased serum total T4 concentrations can reflect, for example, either on excess T4 supply or an excess of TBG binding sites. Conversely, decreased serum total T4 concentrations can occur in association with both a decreased supply of T4 and a decrease in the number or availability of T4 binding sites on TBG. Measurement of the T3 uptake is one means of resolving the diagnostic ambiguity of total T4 and T3 measurements. The T3 uptake value varies inversely with the concentration of unoccupied or available T4 binding sites. Hence, values are elevated in hyperthyroidism, where total serum T4 is high, and also in states of TBG deficiency, where total serum T4 concentration is low. Conversely, T3 uptake values are low in hypothyroidism, where total serum T4 is low, and also in states associated with TBG excess, where total serum T4 is high. Thus, in primary thyroid diseases, deviations from normal in the total serum T4 and the T3 uptake are concordant, while in disorders of hormone binding they are discordant.

In carrying out conventional radioimmunoassay (RIA) procedures for determining T3 uptake, it is essential to employ control sera which are representative of euthyroid, hypothyroid, and hyperthyroid sera. Hypothyroid control sera, which contain amounts of T3 and T4 substantially lower than normal for the test population as a whole and which at the same time have T3 uptake values of the desired magnitude for use as controls (e.g., 15–25% uptake, preferably 17 to 24%) are very difficult to obtain. It has been proposed to prepare hypothyroid controls by stripping T3 and T4 from normal sera, as described for example in Eisentraut U.S. Pat. No. 3,776,698 issued Dec. 4, 1973, Turner et al. U.S. Pat. No. 3,922,145 issued Nov. 25, 1975, and Hollander U.S. Pat. No. 3,928,553 issued Dec. 23, 1975. However, such stripped sera display poor stability during storage. Moreover, because of changes in various endogenous proteins in such stripped sera during storage as well as the changes caused by the stripping procedure itself, the T3 and T4 binding capacity of the stripped sera is greatly reduced, so that the T3 uptake value of the sera is normally too high to be useful as a hypothyroid control even though the T3 and T4 content of the sera is low.

The present invention provides a hypothyroid control serum having improved stability during storage and a T3 uptake value within the desired range by substituting a low-affinity T3 antiserum for the T3, T4 and TBG present in serum such as normal human serum. The T3 antiserum employed as the surrogate must have an affinity much lower than that of the T3 antiserum employed as the reagent antiserum in the assay, so low that it has no practical use as reagent antiserum, in order for it successfully to be used to mimic the characteristics and behavior of natural proteins measured as T3 uptake in hypothyroid serum obtained directly from animal or human sources.

Accordingly, the invention comprises a hypothyroid control serum for use in thyroid function assay of serum with reagent antiserum, said control serum comprising (a) serum from which T3, T4 and TBG have been stripped and (b) a T3 antiserum having an affinity less than 15%, preferably less than 10%, of the affinity of reagent antiserum. The affinity or avidity of the T3 antiserum is measured in terms of the affinity constant of the binding reaction. Since the reagent antiserum normally has an affinity at least as great as $10^9$ liter/mole, the T3 antiserum should in general have an affinity no greater than about $10^{8.2}$ liter/mole, preferably not greater than $10^8$ liter/mole in order to avoid excessive interference. The amount of T3 antiserum added to the stripped serum varies depending upon the T3 uptake value of the stripped serum and upon the desired T3 uptake value of the finished control serum. In general, the finished control serum should have a T3 uptake value from 15 to 25%, preferably from 17 to 24%, as pointed out above. It also preferably has a protein content approximately the same as that of normal human serum which is approximately 70 mg/ml, although it may vary from 68 to 72 mg/ml.

The titer or concentration of the hypothyroid control may be adjusted to the desired level by concentrating the stripped serum by conventional procedures, e.g., by ultrafiltration through a permeable membrane and/or by dilution of the T3 antiserum with a conventional buffer such as phosphate buffered saline solution.

The T3 antiserum can be raised in any mammal, animal or human, by conventional immunological procedures followed by measurement of affinity to ensure that it has the necessary low value. Many such antisera are available as discards from efforts to produce high-affinity T3 antisera for use as reagent sera for assaying T3 uptake.

The stripped serum is made by conventional stripping procedures applied to serum, preferably human serum, which may contain any amount of T3, T4 and TBG, e.g., normal human serum. For use in the hypothyroid control serum of the present invention, the stripped serum preferably contains no detectable amount of T4, that is, no more than 0.05% T4 at most.

In carrying out an immunoassay for thyroid function using the hypothyroid control of the present invention, for example, in assaying T3 uptake value, there may be employed test tubes having a coating of reagent T3 rabbit antiserum bonded to their inner faces, this reagent antiserum having an affinity of $10^9$ liter/mole or more. Into separate tubes are placed appropriate specimens of the unknown test serum and of hypothyroid control. To each tube is added an equal amount of a buffer solution of $^{125}$I-triiodothyronine tracer, after which tubes are incubated at room temperature for approximately an hour. The solutions are then removed from the tubes by aspiration or decanting, after which the tubes are counted in a gamma counter for one minute. The T3 uptake of the test specimen is then calculated from the known T3 uptake value of the hypothyroid control by applying the ratio of the counts for the wo tubes. It will be understood that other controls such as euthyroid and hyperthyroid controls may also be employed in addition to or in place of hypothyroid controls in such an assay, as desired.

It is also possible to conduct an immunoassay for thyroid function by comparing the values obtained from unknown test sera with those obtained from a hypothyroid control serum using as the hypothyroid control serum an antiserum against T3 alone, which antiserum has an affinity no greater than $10^8$ liter/mole, without employing with it any serum from which T3 and T4 have been stripped, although this procedure is not preferred.

The following example is intended to illustrate more fully the nature of the present invention without acting as a limitation upon its scope.

EXAMPLE

To a one-liter specimen of normal human serum is added 35 gm of activated charcoal (Norit EXW) and the specimen is placed in a sealed container and agitated on rollers for 16 hours at ambient temperature. The serum is then centrifuged at 3500 RPM for 20 minutes, and finally filtered stepwise under nitrogen at 20 psi through a succession of filters of decreasing pore size ranging from $20\mu$ pore diameter in the first to $0.22\mu$ in the last. There is then added 0.5 gm/l of sodium azide as preservative and stabilizer, and the pH is adjusted to $7.4\pm0.1$ with concentrated sodium hydroxide or glacial acetic acid, as required. This serum has a T3 uptake value of approximately 40% and a protein content of approximately 40 mg/ml. The serum is then concentrated to a protein content of approximately 70 mg/ml by passing it under pressure across a permeable membrane which retains proteins while permitting permeation of water and low molecular weight materials, and its T3 uptake is again assayed by conventional radioimmunoassay procedure and found to be 26.5%. Residual T4 in this charcoal stripped serum is less than 0.05%.

A T3 antiserum is raised in animals by conventional injection procedures, and after bleeding, the serum is separated and specimens are pooled. The pooled antiserum is determined to have an affinity constant of $10^8$ liter/mole, too low for use as reagent antiserum in a conventional radioimmunoassay procedure. Aliquots of this T3 antiserum are diluted with varying amounts of phosphate buffered saline having the following composition: NaCl 0.15M, KH$_2$PO$_4$ 0.001M, K$_2$HPO$_4$ 0.009M, Na$_2$EDTA 0.37 gm/l, NaN$_3$ 1.25 gm/l and a pH of 7.4. Each aliquot is then mixed with a specimen of the stripped serum and the T3 uptake of each mixture is assayed in order to determine the relative proportions of T3 antiserum and of charcoal stripped serum required to produce an antiserum having a T3 uptake within the desired range, from 15 to 25%. In a typical case, 25 $\mu$l of T3 antiserum mixed with 1 liter of charcoal stripped serum decreases the T3 uptake value of the latter by 1%. Consequently, in order to decrease the T3 uptake value of the stripped serum described above to 21% from 26.5%, it is necessary to add approximately 137 $\mu$l of the T3 antiserum to each liter of stripped serum.

Mixtures of T3 antiserum and charcoal stripped serum prepared as described above having various T3 uptake values from approximately 15% to 25% demonstrate excellent stability upon storage for periods up to four months at temperatures from $-20°$ C. to $37°$ C. and they are suitable for use as hypothyroid control sera in conventional thyroid function assays of human sera.

We claim:

1. Hypothyroid control serum for use in thyroid function assay of serum with reagent antiserum, said control serum comprising serum from which T3 and T4 have been stripped, and antiserum to T3 having an affinity less than 15% of the affinity of said reagent antiserum.

2. Hypothyroid control serum as claimed in claim 1 in which said T3 antiserum has an affinity no greater than 10% of the affinity of said reagent antiserum.

3. Hypothyroid control serum as claimed in claim 1 or 2 having a T3 uptake value from 15 to 25%.

4. Hypothyroid control serum as claimed in claim 1 in which said T3 antiserum has an affinity no greater than $10^{8.2}$ liter/mole.

5. Hypothyroid control serum as claimed in claim 1 in which said T3 antiserum has an affinity no greater than $10^8$ liter/mole.

6. Hypothyroid control serum as claimed in claim 4 or 5 having a T3 uptake value from 15 to 25%.

7. In an immunoassay for thyroid function by comparing the values obtained from unknown test sera with those obtained from a hypothyroid control serum, the step which comprises using as the hypothyroid control serum an antiserum against T3, which antiserum has an affinity no greater than $10^{8.2}$ liter/mole.

8. A method as claimed in claim 7 in which said antiserum has a T3 uptake value of 15 to 25% and a protein content of approximately 70 mg/ml.

9. A method as claimed in claim 7 in which said control serum includes in addition a serum from which T3 and T4 have been stripped.

* * * * *